(12) United States Patent
Gestetner

(10) Patent No.: US 9,167,956 B2
(45) Date of Patent: Oct. 27, 2015

(54) ENDOSCOPE SHEATH

(71) Applicant: Gerald Gestetner, Montreal (CA)

(72) Inventor: Gerald Gestetner, Montreal (CA)

( * ) Notice: Subject to any disclaimer, the term of this patent is extended or adjusted under 35 U.S.C. 154(b) by 45 days.

(21) Appl. No.: 14/106,847

(22) Filed: Dec. 15, 2013

(65) Prior Publication Data
US 2014/0171740 A1    Jun. 19, 2014

Related U.S. Application Data

(60) Provisional application No. 61/738,164, filed on Dec. 17, 2012.

(51) Int. Cl.
*A61B 1/04* (2006.01)
*A61B 1/00* (2006.01)

(52) U.S. Cl.
CPC ............ *A61B 1/00142* (2013.01); *A61B 1/0008* (2013.01); *A61B 1/0011* (2013.01)

(58) Field of Classification Search
USPC ................................................. 600/121–125
See application file for complete search history.

(56) References Cited

U.S. PATENT DOCUMENTS

| | | | | |
|---|---|---|---|---|
| 4,823,949 | A * | 4/1989 | Bala | 206/306 |
| 4,846,344 | A * | 7/1989 | Bala | 206/306 |
| 5,069,337 | A * | 12/1991 | Bala | 206/306 |
| 5,406,939 | A | 4/1995 | Bala | |
| 6,224,543 | B1 * | 5/2001 | Gammons et al. | 600/124 |
| 6,305,536 | B1 * | 10/2001 | Tanaka | 206/316.2 |
| 7,357,788 | B2 * | 4/2008 | Gammons | 604/171 |
| 7,611,010 | B2 * | 11/2009 | Gammons | 206/320 |
| 2005/0177025 | A1 * | 8/2005 | Jaker et al. | 600/121 |
| 2014/0046137 | A1 * | 2/2014 | Brown | 600/203 |

* cited by examiner

*Primary Examiner* — Matthew J Kasztejna

(57) ABSTRACT

An endoscope sheath, said endoscope sheath comprising: a first sheet and a second sheet, said first sheet defining a first sheet distal end and an opposed first sheet proximal end, said first sheet also defining opposed first sheet first and second side edges extending between said first sheet proximal and distal ends, said second sheet defining a second sheet distal end and an opposed second sheet proximal end, said second sheet also defining opposed second sheet first and second side edges extending between said second sheet proximal and distal ends, said first and second sheets being sealed to each other adjacent said first and second sheet distal ends, first side edges and second side edges, said first and second sheets being unsealed from each other adjacent said first and second sheets proximal ends, said first sheet having greater optical clarity than said second sheet adjacent said first and second sheet distal ends, said first sheet being more rigid than said second sheet adjacent said first and second sheet distal ends.

7 Claims, 1 Drawing Sheet

ENDOSCOPE SHEATH

FIELD OF THE INVENTION

The present invention relates to the general field of medical devices, and is more specifically concerned with an endoscope sheath.

BACKGROUND

Endoscope sheaths are used to cover the part of an endoscope that enters the body of a patient in many medical and dental applications. The endoscope includes a lens at its distal end. If the sheath does not abut against the whole lens, the image quality can suffer. One manner of solving this problem is to provide sheaths that are about the same size and shape as the endoscope. However, this can make introduction of the endoscope in the sheaths difficult to perform.

Against this background, there exists a need in the industry to provide an improved endoscope sheath. An object of the present invention is therefore to provide such an endoscope sheath.

SUMMARY OF THE INVENTION

In a broad aspect, the invention provides an endoscope sheath, the endoscope sheath comprising: a first sheet and a second sheet, the first sheet defining a first sheet distal end and an opposed first sheet proximal end, the first sheet also defining opposed first sheet first and second side edges extending between the first sheet proximal and distal ends, the second sheet defining a second sheet distal end and an opposed second sheet proximal end, the second sheet also defining opposed second sheet first and second side edges extending between the second sheet proximal and distal ends, the first and second sheets being sealed to each other adjacent the first and second sheet distal ends, first side edges and second side edges, the first and second sheets being unsealed from each other adjacent the first and second sheets proximal ends, the first sheet having greater optical clarity than the second sheet adjacent the first and second sheet distal ends, the first sheet being more rigid than the second sheet adjacent the first and second sheet distal ends.

In some embodiments of the invention, the first sheet has greater optical clarity than the second sheet over their entire lengths and the first sheet is more rigid than the second sheet over their entire lengths.

In a variant, the first sheet has an elastic modulus that is at least four times that of the second sheet. In another variant, the first sheet has an elastic modulus that is at least ten times that of the second sheet. Other variants are also within the scope of the invention.

In some embodiments of the invention, the endoscope sheath includes a tapered section tapering in a direction leading towards the first and second sheets distal ends. The tapered section extends over at least a portion of the endoscope sheath.

Advantageously, the proposed endoscope sheath can provide a better contact between the first sheet and the lens of an endoscope if the endoscope sheath is properly dimensioned. Indeed, if the second sheet needs to stretch to accommodate insertion of the endoscope through the proximal end of the endoscope sheath, the second sheet will deform and bias the endoscope lens against the first sheet. This improves image quality. Also, this facilitates quick insertion of the endoscope in the endoscope sheath.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
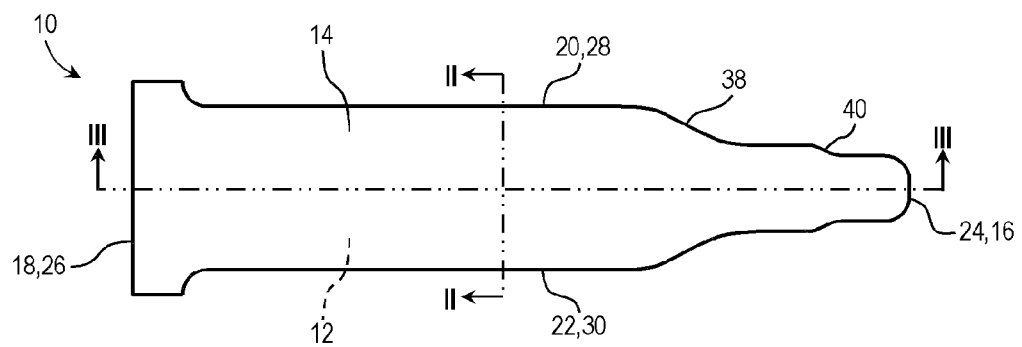
FIG. 1, in a top plan view, illustrates an endoscope sheath in accordance with an embodiment of the present invention.
Figure 2:
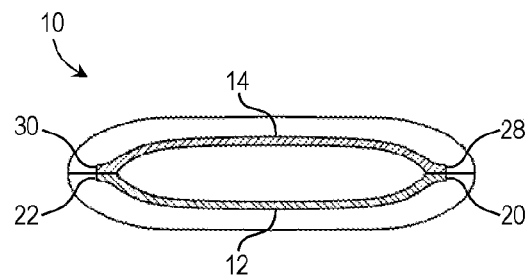
FIG. 2, in front cross-sectional view along section line II-II of FIG. 1, illustrates the endoscope sheath shown in FIG. 1.

Referring to FIG. 1, there is shown an endoscope sheath 10 in accordance with an embodiment of the present invention. As seen in FIG. 2, the endoscope sheath includes a first sheet 12 and a second sheet 14.

Returning to FIG. 1, the first sheet 12 defines a first sheet distal end 16 and an opposed first sheet proximal end 18. The first sheet 12 also defines opposed first sheet first and second side edges 20 and 22 extending between the first sheet proximal and distal ends 18 and 16.

The second sheet 14 defines a second sheet distal end 24 and an opposed second sheet proximal end 26. The second sheet 14 also defines opposed second sheet first and second side edges 28 and 30 extending between the second sheet proximal and distal ends 26 and 24.

The first and second sheets 12 and 14 are sealed to each other adjacent the first and second sheet distal ends 16 and 24, first side edges 20 and 28 and second side edges 22 and 30. The first and second sheets 12 and 14 are unsealed from each other adjacent the first and second sheets proximal ends 18 and 26. Sealing can be performed in any conventional manner, such as by using an adhesive, thermal bonding and ultrasonic welding, among others.

The first sheet 12 has greater optical clarity than the second sheet 14 adjacent the first and second sheet distal ends 16 and 24. Also, the first sheet 12 is more rigid than the second sheet 14 adjacent the first and second sheet distal ends 16 and 24. In some embodiments of the invention, the entire first sheet 12 has greater optical clarity than the entire second sheet 14 and the entire first sheet 12 is more rigid than the entire second sheet 14.

In a variant, the first sheet 12 has an elastic modulus that is at least four times the elastic modulus of the second sheet 14. In a variant, the first sheet 12 has an elastic modulus that is at least ten times the elastic modulus of the second sheet 14.

For example the first sheet 21 is made out of a 3 mil thick flexible PVC film and the second sheet is made out of a 3 mil thick aromatic polyether polyurethane film. However, other materials and thicknesses are within the scope of the invention.

Figure 3:
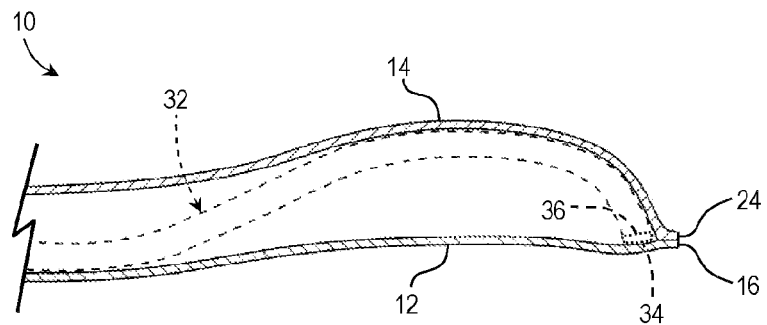
FIG. 3, in side cross-sectional view along section line III-III of FIG. 1, illustrates the endoscope sheath shown in FIG. 1 with an endoscope inserted therein.

In use, as shown in FIG. 3, an endoscope 32 defining an endoscope distal end 34 is inserted in the endoscope sheath 10. The endoscope 32 includes a lens 36 and is inserted with the lens 36 facing the first sheet 12. The first sheet 12 is stretched to a greater extent than the second sheet 14 when the endoscope 32 is inserted in the endoscope sheath 10, which biases the lens 36 against the first sheet 12.

In some embodiments of the invention, the endoscope sheath 10 defines a tapered section 38 adjacent the first and second sheets distal ends 16 and 24. Tapering of the endoscope sheath, along with the mechanical properties of the first and second sheets 12 and 14, creates a synergistic effect that results in ease of insertion of the endoscope 32 in the endoscope sheath 10, while creating a relatively large biasing force to bias the lens 36 against the first sheet 12. This configuration also allows fitting of the endoscope sheath 10 to a relatively large number of models of endoscopes 32. In some embodiments of the invention, the endoscope sheath 10 defines another tapered section 40 adjacent the first and second sheets distal ends 16 and 24 and between the tapered section 38 and the first and second sheets distal ends 16 and 24, which enhances the above-mentioned advantages of the tapered section 38.

Although the present invention has been described hereinabove by way of preferred embodiments thereof, it can be modified, without departing from the spirit and nature of the subject invention as defined in the appended claims.

What is claimed is:

1. An endoscope sheath, said endoscope sheath comprising: a first sheet and a second sheet, said first sheet defining a first sheet distal end and an opposed first sheet proximal end, said first sheet also defining opposed first sheet first and second side edges extending between said first sheet proximal and distal ends, said second sheet defining a second sheet distal end and an opposed second sheet proximal end, said second sheet also defining opposed second sheet first and second side edges extending between said second sheet proximal and distal ends, said first and second sheets being sealed to each other adjacent said first and second sheet distal ends, first side edges and second side edges, said first and second sheets being unsealed from each other adjacent said first and second sheets proximal ends, said first sheet having greater optical clarity than said second sheet adjacent said first and second sheet distal ends, said first sheet having a first sheet elastic modulus that is larger than a second sheet elastic modulus of said second sheet adjacent said first and second sheet distal ends which biases a lens of an endoscope against the first sheet, when the endoscope is inserted into the endoscope sheath.

2. The endoscope sheath as defined in claim 1, wherein said first sheet elastic modulus is at least four times said second sheet elastic modulus.

3. The endoscope sheath as defined in claim 1, wherein said first sheet elastic modulus is at least ten times said second sheet elastic modulus.

4. The endoscope sheath as defined in claim 1, wherein said first sheet is made out of flexible PVC film and said second sheet is made out aromatic polyether polyurethane film.

5. The endoscope sheath as defined in claim 4, wherein said first and second sheets have equal thicknesses.

6. The endoscope sheath as defined in claim 1, wherein said endoscope sheath defines a first tapered section adjacent said first and second sheet distal ends.

7. The endoscope sheath as defined in claim 6, wherein said endoscope sheath defines a second tapered section adjacent said first and second sheet distal ends and between said first tapered section and said first and second sheets distal ends.

* * * * *